(12) United States Patent
Baek et al.

(10) Patent No.: US 12,070,447 B2
(45) Date of Patent: Aug. 27, 2024

(54) PARENTERAL LIQUID PREPARATION COMPRISING CARBAMATE COMPOUND

(71) Applicant: SK BIOPHARMACEUTICALS CO., LTD., Gyeonggi-do (KR)

(72) Inventors: Myoung Ki Baek, Gyeonggi-do (KR); Ji Hye Lee, Gyeonggi-do (KR); So Young Choi, Gyeonggi-do (KR)

(73) Assignee: SK BIOPHARMACEUTICALS CO., LTD., Gyeonggi-do (KR)

( * ) Notice: Subject to any disclaimer, the term of this patent is extended or adjusted under 35 U.S.C. 154(b) by 14 days.

(21) Appl. No.: 16/468,756

(22) PCT Filed: Dec. 14, 2017

(86) PCT No.: PCT/KR2017/014727
§ 371 (c)(1),
(2) Date: Jun. 12, 2019

(87) PCT Pub. No.: WO2018/111000
PCT Pub. Date: Jun. 21, 2018

(65) Prior Publication Data
US 2019/0314336 A1    Oct. 17, 2019

(30) Foreign Application Priority Data

Dec. 14, 2016 (KR) .......................... 10-2016-0170389

(51) Int. Cl.
*A61K 31/41* (2006.01)
*A61K 9/00* (2006.01)
*A61K 9/19* (2006.01)
*A61K 47/40* (2006.01)

(52) U.S. Cl.
CPC ............ *A61K 31/41* (2013.01); *A61K 9/0019* (2013.01); *A61K 47/40* (2013.01)

(58) Field of Classification Search
CPC ...... A61K 31/41; A61K 31/325; A61K 47/40; A61K 9/0019; A61K 9/08; A61K 9/00
See application file for complete search history.

(56) References Cited

U.S. PATENT DOCUMENTS 9,629,797 B2 *  4/2017  Cloyd ................. C08B 37/0012
2006/0258718 A1   11/2006  Choi et al.

FOREIGN PATENT DOCUMENTS

| WO | WO-2006/112685 A1 | 10/2006 |
| WO | WO-2010/150946 A1 | 12/2010 |
| WO | WO-2011/046380 A2 | 4/2011 |

OTHER PUBLICATIONS

Bender (Cyclodextrin Chemistry, Reactivity and Structure Comcepts in Organic Chemistry 6, Springer-Verlag Berlin Heidelberg New York 1978).*

(Continued)

*Primary Examiner* — Jeffrey S Lundgren
*Assistant Examiner* — Heather Raquel Dahlin
(74) *Attorney, Agent, or Firm* — Harness, Dickey & Pierce, P.L.C.

(57) ABSTRACT

The present invention relates to a parenteral liquid preparation containing, as active ingredients; a carbamate compound of chemical formula 1, an isomer thereof, or a pharmaceutically acceptable salt, a solvate or a hydrate thereof; and a cyclodextrin derivative.

5 Claims, 1 Drawing Sheet

(56) References Cited

OTHER PUBLICATIONS

Cavitron (Cavitron™ and Cavasol hydroxypropyl-β-cyclodextrins, Jul. 25, 2012, PC_11734_Cavitron_Cavasol.pdf (ashland.com)(hereinafter Cavitron)).*
Bialer M, Johannessen SI, Levy RH, Perucca E, Tomson T, White HS. Progress report on new antiepileptic drugs: a summary of the Tenth Eilat Conference (EILAT X). Epilepsy research. Dec. 1, 2010;92(2-3):89-124. (Year: 2010).*
Strickley RG. Solubilizing excipients in oral and injectable formulations. Pharmaceutical research. Feb. 2004;21:201-30. (Year: 2004).*
Gershanik, J., et al.; "The Gasping Syndrome and Benzyl Alcohol Poisoning", The New England Journal of Medicine, Nov. 25, 1982, vol. 307, No. 22, pp. 1384-1388.
Irie, T., et al.; "Pharmaceutical Applications of Cyclodextrins. III. Toxicological Issues and Safety Evaluation", Journal of Pharmaceutical Sciences, Feb. 1997, vol. 86, No. 2, pp. 147-162.
Fairchild, E. J., et al.; "Registry of Toxic Effects of Chemical Substances", 1977 Edition, vol. II. DHEW Publ. No.(NIOSH) 78-104-B. (English Abstract Only).
International Search Report (ISR) from corresponding PCT Application No. PCT/KR2017/014727, mailed Feb. 28, 2018.
Rajewski, R. A., et al; "Pharmaceutical Applications of Cyclodextrins. 2. In Vivo Drug Delivery", Journal of Pharmaceutical Sciences, 1996, vol. 85, No. 11, pp. 1142-1169.
Loscher, W., et al.; "New Injectable Aqueous Carbamazepine Solution Through Complexing with 2-Hydroxypropyl-β-Cyclodextrin: Tolerability and Pharmacokinetics After Intravenous Injection in Comparison to a Glycofurol-Based Formulation", Epilepsia, 1995, vol. 36, No. 3, pp. 255-261.
Gould, S., et al.; "2-Hydroxypropyl-β-cyclodextrin (HP-β-CD): a Toxicology Review", Food and Chemical Toxicology, 2005, vol. 43, pp. 1451-1459.
Holvoet, C., et al.; "Inclusion Complexation of Lorazepam with Different Cyclodextrins Suitable for Parenteral Use", Drug Development and Industrial Pharmacy, 2005, vol. 31, pp. 567-575.
Extended European Search Report, dated May 29, 2020 from corresponding European Patent Application No. 17880335.9.
Duncan P Taylor: "YKP3089 (Epilepsy)—Poster", May 24, 2013, XP055650994, Retrieved from the internet: URL:http://www.kddf.org/common/file/?idx=1417&fname=Bio_USA-Poster_10_YKP_3089.pdf [retrieved on—Dec. 9, 2019J].
Examination Report from corresponding Australian Patent Application No. 2017374450, dated Oct. 28, 2022.
Krauss, G., et al.; "Seizure Freedom with YKP3089 as Adjunctive Therapy for Refractory Partial-Onset Seizures in Double-Blind Placebo-Controlled Trials", Neurology, 2016, vol. 86, 16 supplement, .3 pages.

* cited by examiner

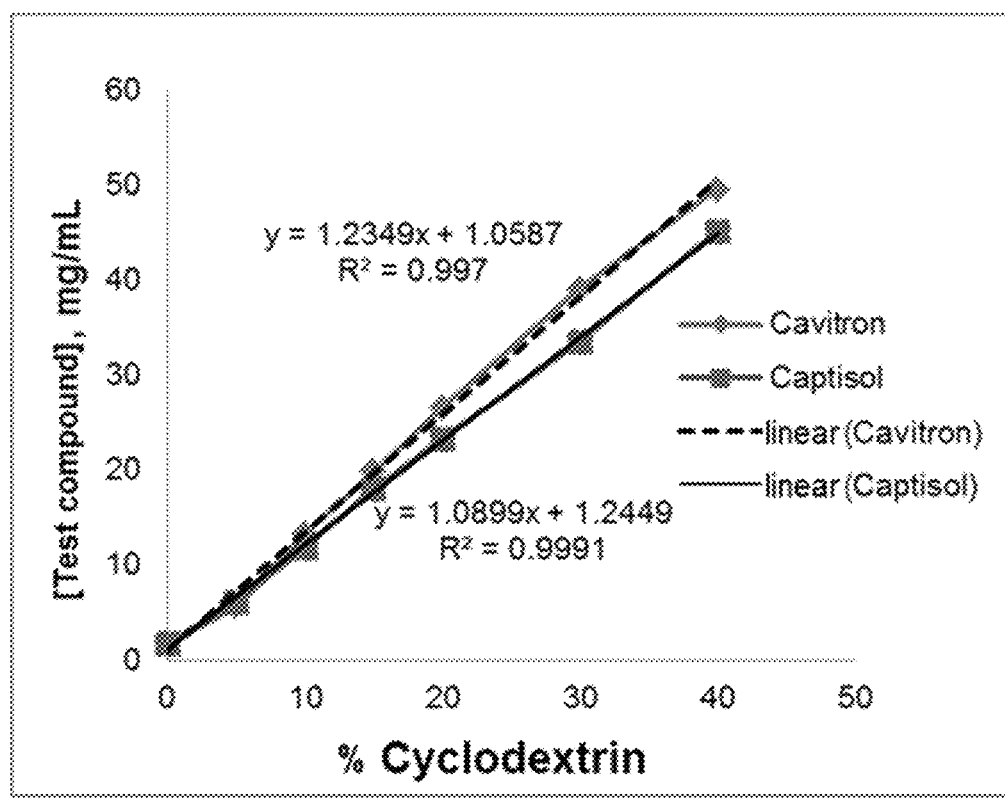

PARENTERAL LIQUID PREPARATION COMPRISING CARBAMATE COMPOUND

CROSS-REFERENCE TO RELATED APPLICATIONS

This application is a national phase application of PCT Application No. PCT/KR2017/014727, filed on 14 Dec. 2017, which claims the benefit and priority to Korean Patent Application No. 10-2016-0170389, filed on 14 Dec. 2016. The entire disclosures of the applications identified in this paragraph are incorporated herein by references.

FIELD

The present invention relates to a parenteral liquid formulation comprising as an active ingredient a carbamate compound of the following Formula 1 or an isomer thereof, or a pharmaceutically acceptable salt, solvate or hydrate thereof; and a cyclodextrin derivative:

[Formula 1]

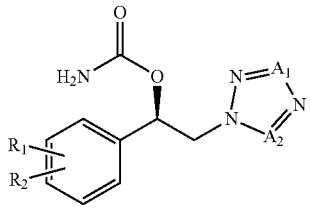

wherein,
$R_1$, $R_2$, $A_1$ and $A_2$ are as defined herein.

BACKGROUND

The carbamate compounds of the above Formula 1 and methods for preparing the same are described in detail in PCT Publication Nos. WO 2006/112685 A1, WO 2010/150946 A1 and WO 2011/046380 A2, the disclosures of which are incorporated herein by reference. One specific embodiment of the carbamate compounds of the above Formula 1 is carbamic acid (R)-1-(2-chlorophenyl)-2-tetrazol-2-yl)ethyl ester of the following Formula 2:

[Formula 2]

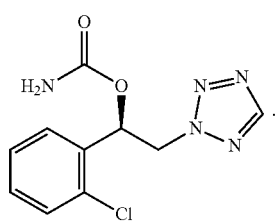

The carbamate compounds of the above Formula 1 are known to be effective anticonvulsants for use in central nervous system diseases.

Oral formulations of the compounds are suitable for repeated administration over an extended treatment period to ensure a uniform concentration of active ingredient in the blood.

However, in emergency situations where symptoms of epilepsy have occurred, oral administration to patients may not be appropriate as first aid. Particularly, patients with epileptic partial seizure usually experience difficulties in controlling symptoms. Because of this, many epilepsy patients need to take more than one anticonvulsant daily. In addition, when the medication being taken is suddenly changed to another medication or its taking is suddenly stopped, not only may symptoms recur, but also a breakthrough seizure may follow, which is an emergency.

The persistent state of epilepsy is an emergent disease that may cause severe aftereffects, and thus quick judgment and treatment of the patient's condition is required. In the persistent state of epilepsy, the longer the seizure duration, the higher the drug resistance and the nerve damage, so the sooner the treatment is started, the better the treatment effect and the prognosis is more likely to improve. The treatment usually consists of securing the airway, maintaining respiration and circulation, and administering a drug by an injection formulation. Hence, there has been a need for parenteral pharmaceutical liquid formulations capable of sustaining treatment in patients with epilepsy who cannot take the drug orally.

A number of methods for preparing injection solutions containing benzyl alcohol, ethanol, surfactants, emulsifiers and the like are known in order to improve the solubility of the active ingredient in water for injection. However, benzyl alcohol and surfactants can cause unwanted side effects. For example, polysorbate 80, alone or in combination with benzyl alcohol, can act as a potent cardiac inhibitor and cause hypertension and cancer (Fairchild, E. J., R. J. Lewis, Jr., and R. L. Tatken (1977), Registry of Toxic Effects of Chemical Substances, 1977 Edition, Volume II. DHEW Publ. No. (NIOSH) 78-104-B.). In addition, parenteral administration of benzyl alcohol involves redness, pain, tissue damage, hemolysis, death and many other side effects (Gershanik J, Boecler B, Ensley H, McCloskey S, George W. The gasping syndrome and benzyl alcohol poisoning, New England Journal of Medicine 1982; 307(22):1384-8). Also, when a compound is dissolved in an organic solvent at a high concentration, the compound may precipitate during long-term storage.

Cyclodextrins are cyclic hydrocarbons derived from starch and possess a hydrophobic (lipophilic) central cavity and a hydrophilic outer surface. There are a number of different cyclodextrin structures in nature, and the most common ones are alpha-cyclodextrin, beta-cyclodextrin and gamma-cyclodextrin, each of which consists of 6, 7 and 8 glucopyranose units, respectively. Cyclodextrins can stabilize a drug by reversibly forming a water-soluble complex with the drug, but it is known that formation of inclusion complexes is not possible or yield is low in many drugs. In addition, its use as an injection is limited due to its limited solubility and side effects such as renal toxicity (T. Irie and K. Uekama, "Pharmaceutical applications of cyclodextrins. III. Toxicological issues and safety evaluation," J. Pharm. Sci., 86(2), 147-162 (1997)).

Thus, with respect to the carbamate compounds of the above Formula 1 or 2, there is a need for development of a liquid formulation without using an organic solvent of an alcohol such as benzyl alcohol or a highly toxic surfactant such as polysorbate 80 which may cause side effects, and that can be administered parenterally to patients who cannot take drugs orally by increasing the water solubility of the above compounds and improving the storage stability.

SUMMARY

Problem to be Solved

Accordingly, the present invention is intended to provide a parenteral liquid formulation containing the carbamate compounds of the above Formula 1 or 2 as an active ingredient and not containing benzyl alcohol and a surfactant at all, wherein said formulation has sufficient solubility even when no heat is applied and has excellent storage stability.

Technical Solution to the Problem

The present inventors have found that addition of a cyclodextrin derivative increases the solubility of the carbamate compound of the above Formula 1 or 2 as an active ingredient in an aqueous solution to an unexpected degree. The present inventors also have found that addition of a cyclodextrin derivative not only improves the solubility of the active ingredient in water, but also improves the storage stability of the thus-obtained parenteral liquid formulation.

Accordingly, the present invention provides a parenteral liquid formulation comprising as an active ingredient a carbamate compound of the following Formula 1 or an isomer thereof, or a pharmaceutically acceptable salt, solvate or hydrate thereof; and a cyclodextrin derivative:

[Formula 1]

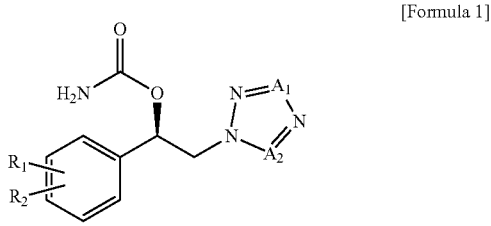

wherein,
$R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and
one of $A_1$ and $A_2$ is CH, and the other is N.

According to one embodiment of the present invention, in the above Formula 1, $R_1$ and $R_2$ are each independently selected from the group consisting of hydrogen, halogen and $C_1$-$C_8$ alkyl.

In one embodiment, the halo $C_1$-$C_8$ alkyl is perfluoroalkyl.

According to another embodiment of the present invention, the carbamate compound of the above Formula 1 is carbamic acid (R)-1-(2-chlorophenyl)-2-tetrazol-2-yl)ethyl ester of the following Formula 2:

[Formula 2]

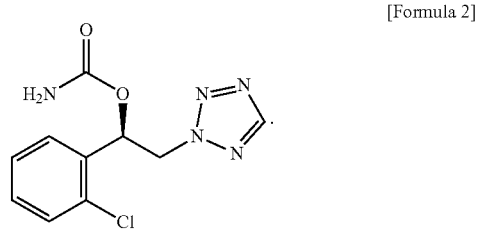 [SMILES: NC(=O)O[C@@H](Cn1ncnn1)c1ccccc1Cl]

In one embodiment of the present invention, the cyclodextrin derivative is a hydroxyalkyl-cyclodextrin or sulfoalkyl ether-cyclodextrin, specifically 2-hydroxypropyl-cyclodextrin or sulfobutyl ether-cyclodextrin.

In one embodiment of the present invention, the parenteral liquid preparation contains the carbamate compounds of Formula 1 in a concentration of 0.5 to 20 mg/ml.

In one embodiment of the present invention, the weight ratio of the carbamate compounds of Formula 1 to the cyclodextrin derivatives is about 1:2 to 1:50, or 1:5 to 1:40, or 1:10 to 1:30, or 1:15 to 1:30.

In one embodiment of the present invention, the formulation contains carbamic acid (R)-1-(2-chlorophenyl)-2-tetrazol-2-yl)ethyl ester and 2-hydroxypropyl-cyclodextrin in the weight ratio of 1:2 to 1:50.

In one embodiment of the present invention, the formulation contains carbamic acid (R)-1-(2-chlorophenyl)-2-tetrazol-2-yl)ethyl ester and sulfobutyl ether-cyclodextrin in the weight ratio of 1:2 to 1:50.

The present invention also provides a parenteral liquid formulation comprising as an active ingredient the carbamate compounds of the above Formula 1 or an isomer thereof, or a pharmaceutically acceptable salt, solvate or hydrate thereof; and a cyclodextrin derivative, for use as an anti-convulsant.

According to one embodiment of the present invention, the parenteral liquid formulation is used for the treatment of anxiety, depression, convulsion, epilepsy, migraine, bipolar disorder, drug abuse, smoking, attention deficit hyperactivity disorder (ADHD), obesity, sleep disorders, neuropathic pain, stroke, cognitive disorders, neurodegeneration and muscle spasm.

The present invention also provides an injectable composition comprising the parenteral liquid formulation.

The present invention also provides a method for preparing a parenteral liquid formulation, comprising mixing the carbamate compounds of the above Formula 1 and the cyclodextrin derivatives in a solvent.

Effect of the Invention

The parenteral liquid formulation according to the present invention can be administered parenterally immediately to patients who cannot orally take the carbamate compounds of the above Formula 1 or 2, so that the drug can be rapidly supplied. In particular, immediate response as an injection is highly desirable in an emergency. Moreover, since the absorption process is not required, the blood concentration of the active ingredient can be obtained accurately and quickly.

In addition, the parenteral liquid formulation according to the present invention can significantly increase the solubility of the active ingredient in an aqueous solution due to the cyclodextrin derivative, thereby reducing the required dose volume and showing a very high storage stability. Furthermore, since an organic solvent of an alcohol such as benzyl alcohol or a highly toxic surfactant such as polysorbate 80 is not used, the parenteral liquid formulation according to the present invention does not cause side effects, which is advantageous in safety.

BRIEF DESCRIPTION OF THE DRAWINGS

FIG. 1 is a graph showing the results of saturation solubility of carbamic acid (R)-1-(2-chlorophenyl)-2-tetrazol-2-yl) ethyl ester according to the concentration of cyclodextrin evaluated in Experimental Example 1.

DETAILED DESCRIPTION

Hereinafter, the present invention will be described in detail.

The present invention relates to a parenteral liquid formulation comprising as an active ingredient a carbamate compound of the following Formula 1 or an isomer thereof, or a pharmaceutically acceptable salt, solvate or hydrate thereof; and a cyclodextrin derivative:

[Formula 1]

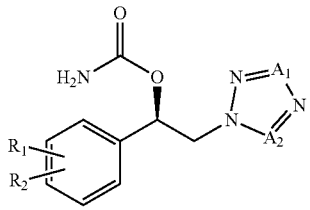

wherein, $R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and one of $A_1$ and $A_2$ is CH, and the other is N.

In one embodiment of the present invention, in the above Formula 1, $R_1$ and $R_2$ are each independently selected from the group consisting of hydrogen, halogen and $C_1$-$C_8$ alkyl.

In one embodiment, the halo $C_1$-$C_8$ alkyl is perfluoroalkyl.

In one embodiment, the carbamate compound of the above Formula 1 is carbamic acid (R)-1-(2-chlorophenyl)-2-tetrazol-2-yl)ethyl ester of the following Formula 2:

[Formula 2]

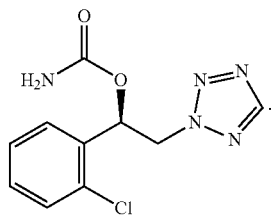

The term "compound" or "active ingredient" is a concept that encompasses not only the compound itself but also its isomers, or pharmaceutically acceptable salts, solvates and hydrates thereof altogether. Accordingly, as used herein, the carbamate compound of the above Formula 1 refers to not only the compound but also its isomers, or pharmaceutically acceptable salts, solvates or hydrates thereof. Likewise, as used herein, the carbamate compound of the above Formula 2 refers to not only the carbamic acid (R)-1-(2-chlorophenyl)-2-tetrazol-2-yl)ethyl ester but also its isomers, or pharmaceutically acceptable salts, solvates or hydrates thereof.

Examples of the pharmaceutically acceptable salts of the carbamate compounds of the above Formula 1 include independently, acetate, benzenesulfonate, benzoate, bitartrate, calcium acetate, camsylate, carbonate, citrate, edetate, edisylate, estolate, esylate, fumarate, gluceptate, gluconate, glutamate, glycoloyl arsanilate, hexylresorcinate, hydravamine, hydrobromide, hydrochloride, hydrogencarbonate, hydroxynaphthoate, iodide, isethionate, lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate or hemi-succinate, sulfate or hemi-sulfate, tannate, tartrate, oxalate or hemi-tartrate, teoclate, triethiodide, benzathine, chloroprocaine, choline, diethanolamine, ethylenediamine, meglumine, procaine, aluminum, ammonium, tetramethylammonium, calcium, lithium, magnesium, potassium, sodium and zinc.

A person having ordinary skill in the art of synthesis of compounds could have easily prepared the carbamate compounds of the above Formulas 1 and 2 using known compounds or compounds which can be easily prepared therefrom. In particular, methods for preparing the compounds of the above Formula 1 are described in detail in PCT Publication Nos. WO 2006/112685 A1, WO 2010/150946 A1 and WO 2011/046380 A2, the disclosures of which are incorporated herein by reference. The compounds of the above Formula 1 can be chemically synthesized by any of the methods described in the above documents, but the methods are merely exemplary ones, and the order of the unit operation and the like may be selectively changed if necessary. Hence, the above methods are not intended to limit the scope of the invention.

However, the solubility of the carbamate compounds of the above Formula 1 or 2 in an aqueous solution is not at a level that can be prepared as an injection. Hence, it is not easy to prepare an injectable preparation for administering a high dose to the human body.

The parenteral liquid formulation according to the present invention comprises the above active ingredients and cyclodextrin derivatives. Types of cyclodextrins include alpha-cyclodextrin, beta-cyclodextrin and gamma-cyclodextrin. The cyclodextrin derivatives include (1) alkylated cyclodextrins, specifically methyl-, dimethyl-, trimethyl- and ethyl-cyclodextrins; (2) hydroxyalkylated cyclodextrins, specifically hydroxyethyl-, hydroxypropyl- and dihydroxypropyl-cyclodextrins; (3) ethyl carboxymethyl cyclodextrin; (4) sulfate, sulfonate and sulfoalkyl cyclodextrins, specifically cyclodextrin sulfate, cyclodextrin sulfonate and sulfobutyl ether-cyclodextrin; (5) polymeric cyclodextrins, or combinations thereof. Preferably, the cyclodextrin derivative may be a hydroxyalkyl-cyclodextrin or sulfoalkyl ether-cyclodextrin, more specifically 2-hydroxypropyl-β-cyclodextrin (HP-β-CD or HPCD, trade name: Cavitron) or sulfobutyl ether-β-cyclodextrin (SAE-β-CD or SAE-CD, trade name: Captisol). In one embodiment, the cyclodextrin derivative may be sulfobutyl ether-7-β-cyclodextrin. As they are safer and have higher solubility in the human body, they can be used as injections (S. Gould and R. C. Scott, "2-Hydroxypropyl-beta-cyclodextrin (HP-beta-CD): a toxicology review," Food Chem Toxicol., 43(10), 1451-1459 (2005)). The sulfoalkyl ether cyclodextrin may be in the form of an alkali metal salt.

The active ingredient and the cyclodextrin derivative form an inclusion complex such that the active ingredient is wholly or partially present inside the cyclodextrin derivative.

The content of the carbamate compounds of the above Formula 1 or 2 in the parenteral liquid formulation may vary depending on the application of the preparation, but is in the range of about 0.5 to 20 mg/ml, preferably about 1 to 15 mg/ml in the total composition.

The parenteral liquid formulation may contain the compound of Formula 1 not contained in the inclusion complex in addition to the compound of Formula 1 contained in the inclusion complex.

The content of the cyclodextrin derivatives in the parenteral liquid formulation also may vary depending on the application of the preparation, but the weight ratio of the compounds to the cyclodextrin derivatives is about 1:2 to 1:50, or 1:5 to 1:40, or 1:10 to 1:30, or 1:15 to 1:30.

According to one embodiment of the present invention, the parenteral liquid formulation of the present invention may contain carbamic acid (R)-1-(2-chlorophenyl)-2-tetrazol-2-yl)ethyl ester of Formula 2 and 2-hydroxypropyl-β-cyclodextrin in the weight ratio of about 1:2 to 1:50, or 1:5 to 1:40, or 1:10 to 1:30, or 1:15 to 1:30. According to another embodiment of the present invention, the parenteral liquid formulation of the present invention may contain carbamic acid (R)-1-(2-chlorophenyl)-2-tetrazol-2-yl)ethyl ester and sulfobutyl ether-β-cyclodextrin alkali metal salt in the weight ratio of about 1:2 to 1:50, or 1:5 to 1:40, or 1:10 to 1:30, or 1:15 to 1:30.

In one embodiment, the liquid formulation may comprise 0.1 to 1.5% by weight of the compound of Formula 1 and 2.5 to 45% by weight of the cyclodextrin derivative. More specifically, the formulation may comprise 0.25 to 1.0% by weight of the compound of Formula 1 and 7.5 to 30% by weight of the cyclodextrin derivative.

The liquid formulation means a preparation in which the active ingredient is dissolved in a solvent such as water. The parenteral liquid formulation may be an injection formulation. Sterile water may be used as a solvent being water. Saline solution, PBS buffer, isotonic water, Ringer's lactate solution, 5% dextrose in water and the like can be used as a solvent other than water. Known solvents used in the manufacture of medicines can be suitably used.

The parenteral liquid formulation may further contain an additive. Any additives that are commonly used in parenteral liquid formulation in the field of pharmaceutical preparations can be suitably used. Specifically, additives include isotonic agents, stabilizers, buffers, preservatives and the like.

Examples of isotonic agents include sugars such as glucose, sorbitol and mannitol, sodium chloride and the like.

Examples of stabilizers include sodium sulfite and the like.

In addition, the parenteral liquid formulation has a pH suitable for administration to the human body without adding a pH adjusting agent, and no significant pH change is observed under the storage conditions. Therefore, a pH adjusting agent may or may not be added to the parenteral liquid formulation. If the pH adjusting agent is not added, the manufacturing process can be simplified, and it is advantageous that there is no need to consider compatibility with the pH adjusting agent. Usable buffers include a borate buffer, a phosphate buffer, a citrate buffer, a tartrate buffer and the like.

Examples of preservatives include parabens (methyl, ethyl, propyl and butyl paraben), paraben sodium salts, potassium sorbate, sodium benzoate and sorbic acid.

The parenteral liquid formulation may be prepared by dissolving the active ingredient, the cyclodextrin derivative and optionally an additive in a solvent. The order of mixing of the above-mentioned ingredients is not critical, but preferably the cyclodextrin derivative is first dissolved in the solvent and then the active ingredient and the remaining additives are added.

The resulting solution can be subjected to filtration sterilization using a membrane filter or sterilization by a pressurized high-temperature sterilization method using an autoclave. More preferably, filtration sterilization is used.

The liquid obtained after the sterilization is filled into the injection ampoule and sealed by careful purging of nitrogen or an inert gas, thereby preventing formation of oxidative decomposition products.

The parenteral liquid formulation can be used as an anticonvulsant, and can be used for the treatment of anxiety, depression, convulsion, epilepsy, migraine, bipolar disorder, drug abuse, smoking, attention deficit hyperactivity disorder (ADHD), obesity, sleep disorders, neuropathic pain, stroke, cognitive disorders, neurodegeneration and muscle spasm.

The dosage of the carbamate compounds of Formula 1 or 2 for the prevention, alleviation or treatment of the above diseases may typically vary depending on the severity of the disease, the body weight and the metabolic status of the subject. A "therapeutically effective amount" for an individual patient refers to an amount of the active compound sufficient to achieve a therapeutic effect. Specifically, the therapeutically effective amount of the compounds of the present invention is 50 to 500 mg, 50 to 400 mg, 50 to 300 mg, 100 to 400 mg, 100 to 300 mg, 50 to 200 mg, or 100 to 200 mg, based on the free form and once-daily administration to humans. The therapeutically effective amount is preferably 50 to 300 mg, more preferably 50 to 200 mg.

The parenteral liquid formulation of the present invention can be administered parenterally, and specifically, it can be administered by intravenous injection, subcutaneous injection, muscle injection, intraperitoneal injection, endothelial administration, topical administration, intranasal administration, intravaginal administration, intrapulmonary administration and rectal administration. Preferably, it can be administered by intravenous injection. The administration route may vary depending on the general condition and age of the subject to be treated, the nature of the treatment condition and the active ingredient selected.

Specifically, the present invention provides an injection composition comprising the above parenteral liquid formulation.

The parenteral liquid formulation has the advantage of delivering 100% of the active ingredient dose to the body in a consistent and predictable manner, differently from oral formulations.

The usage and dosage of the pharmaceutical parenteral liquid formulation of the present invention are determined depending on the gender, age and other conditions, the disease state and the like of the patient. In one embodiment, the parenteral liquid formulation of the present invention may be administered in a single dose or multi-dose. Specifically it can be administered one to three times a day at 8 to 24 hour intervals in a single dose, and the dosage and interval may be adjusted as necessary.

The parenteral liquid formulation according to the present invention can be administered parenterally immediately to patients who cannot orally take the carbamate compounds of the above Formula 1 or 2, so that the drug can be rapidly supplied. In particular, immediate response as an injection is highly desirable in an emergency. Moreover, since the absorption process is not required, the blood concentration of the active ingredient can be obtained accurately and quickly In addition, the cyclodextrin derivative in the parenteral liquid formulation according to the present invention can increase the solubility of the active ingredient in an aqueous solution, thereby reducing the required dose volume and showing high storage stability. Furthermore, since an organic solvent of an alcohol such as benzyl alcohol or a highly toxic surfactant such as polysorbate 80 is not used, the parenteral liquid formulation according to the present invention does not cause side effects, which is advantageous in safety.

Hereinafter, the present invention will be explained in more detail through working examples. However, the following working examples are only intended to illustrate one or more embodiments and are not intended to limit the scope of the invention.

EXAMPLES

Preparation Example: Synthesis of carbamic acid (R)-1-(2-chlorophenyl)-2-tetrazol-2-yl)ethyl ester Carbamic acid (R)-1-(2-chlorophenyl)-2-tetrazol-2-yl) ethyl ester (the compound of Formula 2, hereinafter referred to as "the test compound") was prepared according to the method described in Preparation Example 50 of PCT Publication No. WO 2010/150946.

Example 1: Preparation of Parenteral Liquid Formulation 225 g of each of 2-hydroxypropyl-β-cyclodextrin (trade name: Cavitron) and sulfobutyl ether-β-cyclodextrin sodium salt (trade name: Captisol) as cyclodextrin compounds was dissolved in 1 L of water for injection to prepare 22.5% (W/V) cyclodextrin solutions. While mixing each solution at room temperature, 10 g of carbamic acid (R)-1-(2-chlorophenyl)-2-tetrazol-2-yl)ethyl ester zol-2-yl) ethyl ester was added to each solution. The mixture was mixed until the active ingredients were completely dissolved, and then the solution was slowly cooled to room temperature. A visually clear and dilutable solution was obtained. The solution was sterilized by filtration through a 0.22 μm filter (polyvinylidene fluoride Durapore hydrophilic membrane) and then filled into the injection ampoule through nitrogen gas purging, followed by sealing.

Experimental Example 1: Determination of Saturation Solubility According to the Concentration of Cyclodextrin Derivative 2-Hydroxypropyl-β-cyclodextrin (trade name: Cavitron) and sulfobutyl ether-β-cyclodextrin sodium salt (trade name: Captisol) as cyclodextrin compounds were each dissolved in water for injection at various concentrations as shown in Table 1. To this was added an excess amount of carbamic acid (R)-1-(2-chlorophenyl)-2-tetrazol-2-yl)ethyl ester, and the mixture was stirred at room temperature for 6 hours. The mixture was then filtered through a membrane filter to remove insolubles, and the amount of carbamic acid (R)-1-(2-chlorophenyl)-2-tetrazol-2-yl)ethyl ester in the filtrate was measured by high performance liquid chromatography, by which the saturation solubility was calculated. The column used in this experiment was a 75×4.6 mm, 3.5 μm C18 column, and the mobile phase was a mixed solution of 20% by volume of acetonitrile and 80% by volume of 10 mM phosphate buffer (pH 3.0). The flow rate was 2.0 mL/min, and detection was performed at 215 nm.

As a comparative example, the saturation solubility of carbamic acid (R)-1-(2-chlorophenyl)-2-tetrazol-2-yl)ethyl ester to which no cyclodextrin compound had been added was measured at room temperature.

The calculated saturation solubility values are shown in Table 1, and the same results are shown graphically in FIG. 1.

TABLE 1

Saturation solubility of carbamic acid (R)-1-(2-chlorophenyl)-2-tetrazol-2-yl)ethyl ester at various concentrations of cyclodextrin derivatives

| Concentrations of cyclodextrin derivatives (% W/V) | Cavitron Solubility (mg/mL) | Captisol Solubility (mg/mL) |
|---|---|---|
| 0 (Comparative Example) | 1.8 | 1.8 |
| 5 | 5.5 | 6.7 |
| 10 | 13.2 | 12.8 |
| 15 | 19.8 | 18.0 |
| 20 | 27.9 | 24.5 |
| 30 | 38.6 | 32.5 |
| 40 | 49.5 | 45.1 |

As shown in Table 1, when the cyclodextrin compound was added, the solubility of the carbamic acid (R)-1-(2-chlorophenyl)-2-tetrazol-2-yl)ethyl ester was significantly improved as compared with the comparative example in which the cyclodextrin compound was not added. It was understood that the improved solubility resulted from the above compound forming a stable inclusion complex with the cyclodextrin derivative. In addition, the solubility of the compound was increased in proportion to the amount of the cyclodextrin compound used.

Experimental Example 2: Determination of Saturation Solubility According to pH Change The solubility of carbamic acid (R)-1-(2-chlorophenyl)-2-tetrazol-2-yl)ethyl ester in various aqueous (water) solvent conditions was measured: (1) purified water, (2) pH 1 hydrochloric acid solution, and (3) pH 3 to 8 phosphate buffer solution. Specifically, about 50 mg of carbamic acid (R)-1-(2-chlorophenyl)-2-tetrazol-2-yl)ethyl ester was placed in a suitable glass vial and 15 mL of solvent was added. The mixture was slowly stirred at room temperature for 12 hours on a rotary stirrer to reach equilibrium. Two samples for each aqueous solvent were transferred to a microtube, and centrifuged, and the pH was measured by taking the supernatant. After dilution with diluted solution for analysis, the concentration was analyzed using high performance liquid chromatography under the same conditions as in Experimental Example 1 above.

TABLE 2

Saturation solubility of carbamic acid (R)-1-(2-chlorophenyl)-2-tetrazol-2-yl)ethyl ester according to pH change

| | | Concentration of carbamic acid (R)-1-(2-chlorophenyl)-2-tetrazol-2-yl)ethyl ester | | |
|---|---|---|---|---|
| Aqueous solution | Final pH | Test solution 1 | Test solution 2 | Mean |
| pH 1 hydrochloric acid solution | — | 1.94 | 1.97 | 1.95 |
| pH 3.0 phosphate buffer solution | 3.1 | 1.87 | 1.86 | 1.87 |
| pH 5.0 phosphate buffer solution | 5.0 | 1.91 | 1.91 | 1.91 |
| pH 6.5 phosphate buffer solution | 6.6 | 1.86 | 1.86 | 1.86 |
| pH 8.0 phosphate buffer solution | 8.0 | 1.80 | 1.82 | 1.81 |
| Purified water | 6.2 | 1.80 | 1.81 | 1.80 |

As shown in Table 2 above, the solubility of the carbamic acid (R)-1-(2-chlorophenyl)-2-tetrazol-2-yl)ethyl ester was not greatly affected by the change in pH. This means that even if a pH adjusting agent is not particularly added in the preparation of the parenteral liquid formulation of the present invention, stability can be achieved. Therefore, the manufacturing process can be simplified, and it is advantageous that there is no need to consider compatibility with the pH adjusting agent Experimental Example 3: Confirmation of Storage Stability The liquid formulation containing 10 mg/mL of carbamic acid (R)-1-(2-chlorophenyl)-2-tetrazol-2-yl)ethyl ester prepared in Example 1 was stored at room temperature for 6 months, and the change in the content of the test compound was measured using high performance liquid chromatography under the same conditions as in Experimental Example 1. The results are shown in Table 3.

TABLE 3

Stability of parenteral liquid formulations for 6 months at room temperature

|  | Cavitron | Captisol |
|---|---|---|
| Initial concentration | 10 mg/mL | 10 mg/mL |
| 1 month, content (%) | 99.8% | 102.5% |
| 3 months, content (%) | 100.7% | 105.1% |
| 6 months, content (%) | 100.4% | 105.2% |

What is claimed is:

1. A parenteral liquid formulation comprising as a sole active ingredient a carbamate compound which is carbamic acid (R)-1-(2-chlorophenyl)-2-tetrazol-2-yl-ethyl ester of the following Formula 2, or a pharmaceutically acceptable salt, solvate or hydrate of the compound of Formula 2; and a cyclodextrin derivative:

[Formula 2]

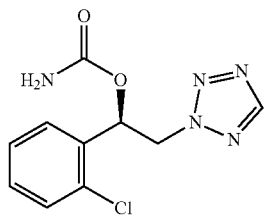

wherein the cyclodextrin derivative is 2-hydroxypropyl-β-cyclodextrin or sulfobutyl ether-β-cyclodextrin, and
wherein a weight ratio of the active ingredient to the cyclodextrin derivative is 1:5 to 1:40; and
wherein the carbamate compound of Formula 2 and the cyclodextrin form an inclusion complex.

2. The parenteral liquid formulation according to claim 1, which contains the carbamate compound of Formula 2 in a concentration of 0.5 mg/ml to 20 mg/ml.

3. The parenteral liquid formulation according to claim 1, which is used as an anticonvulsant.

4. The parenteral liquid formulation according to claim 1, which is used for the treatment of anxiety, depression, convulsion, epilepsy, migraine, bipolar disorder, drug abuse, smoking, attention deficit hyperactivity disorder (ADHD), obesity, sleep disorders, neuropathic pain, stroke, cognitive disorders, neurodegeneration and muscle spasm.

5. An injection composition comprising a parenteral liquid formulation according claim 1.

* * * * *